(12) United States Patent
Christmas (10) Patent No.: US 11,065,465 B2
(45) Date of Patent: Jul. 20, 2021

(54) DEFIBRILLATOR COVER

(71) Applicant: Gregory Christmas, San Diego, CA (US)

(72) Inventor: Gregory Christmas, San Diego, CA (US)

( * ) Notice: Subject to any disclaimer, the term of this patent is extended or adjusted under 35 U.S.C. 154(b) by 113 days.

(21) Appl. No.: 16/226,349

(22) Filed: Dec. 19, 2018

(65) Prior Publication Data

US 2019/0175928 A1    Jun. 13, 2019

Related U.S. Application Data

(63) Continuation-in-part of application No. 29/628,915, filed on Dec. 8, 2017, now Pat. No. Des. 839,433.

(51) Int. Cl.
*A61N 1/39* (2006.01)

(52) U.S. Cl.
CPC ......... *A61N 1/3968* (2013.01); *A61N 1/3993* (2013.01); *A61N 1/3904* (2017.08); *A61N 1/3925* (2013.01)

(58) Field of Classification Search
CPC .. A61N 1/3904; A61N 1/3968; A61N 1/3993; A61B 50/00; A61B 2050/105; A45C 11/00; B65D 77/00; B65D 77/20
See application file for complete search history.

(56) References Cited

U.S. PATENT DOCUMENTS

| | | | |
|---|---|---|---|
| D305,648 S | 1/1990 | Edington | |
| 5,894,878 A | 4/1999 | Morgan et al. | |
| D410,450 S | 6/1999 | Solero | |
| 6,132,367 A * | 10/2000 | Adair | A61B 1/00039 206/438 |
| D454,882 S | 3/2002 | Jung | |
| 6,422,669 B1 * | 7/2002 | Salvatori | A61N 1/3904 312/213 |
| D614,772 S | 4/2010 | Buchanan et al. | |
| D774,036 S | 12/2016 | Kuntz et al. | |
| D781,863 S | 3/2017 | Lai et al. | |
| D803,212 S | 11/2017 | Smit | |
| 2004/0090427 A1 * | 5/2004 | Blair | G06F 3/04886 345/173 |
| 2007/0009698 A1 * | 1/2007 | Hoheisel | A61B 46/10 428/40.1 |
| 2011/0130798 A1 * | 6/2011 | Elghazzawi | G09G 3/00 607/5 |
| 2015/0045845 A1 * | 2/2015 | Albright | B65D 77/204 607/4 |
| 2017/0252571 A1 * | 9/2017 | Dascoli | A61N 1/3987 |

* cited by examiner

*Primary Examiner* — Allen Porter
(74) *Attorney, Agent, or Firm* — Lewis Roca Rothgerber Christie LLP (57) ABSTRACT

A defibrillator and a cover adhered to the defibrillator is provided. The defibrillator includes: a case; a handle at an upper surface of the case; a display panel at a front face of the case; and a plurality of buttons at the front face of the case. The cover covers the display panel and at least some of the buttons, and the cover includes a flexible plastic film.

13 Claims, 7 Drawing Sheets

DEFIBRILLATOR COVER

CROSS-REFERENCE TO RELATED APPLICATION

This application is a continuation-in-part of U.S. application Ser. No. 29/628,915, filed on Dec. 8, 2017 in the U.S. Patent and Trademark Office, the entire content of which is incorporated herein by reference.

BACKGROUND

1. Field

Aspects of embodiments of the present invention are directed toward a defibrillator with a cover adhered thereto and a method of installing the cover onto the defibrillator.

2. Description of Related Art

The human heart beats according to electrical signals (or impulses) output by the sinus node that control the various parts of the heart, ensuring the heart beats at a proper rate and in proper form. A heart arrhythmia occurs when there is a disruption in these electrical signals, which causes the heart to beat too fast (tachycardia) or too slow (bradycardia).

A defibrillator is a medical device that delivers an electric current (often referred to as an electric shock) to a patient suffering from an arrhythmia. Specifically, a defibrillator is used to correct a patient's dysrhythmia, such as ventricular fibrillation (VF) and non-perfusing ventricular tachycardia (VT). Defibrillators are used at one step in cardiopulmonary resuscitation (CPR).

One cause of heart arrhythmia is traumatic injury, such as a car accident, violent crime, etc. For at least this reason, first-responders, such as Emergency Medical Technicians (EMTs), and other health care providers that treat trauma patients, including emergency room doctors and nurses, often employ defibrillators to restore patients' heart rhythms.

Often, accident scenes, such as car accidents, and emergency rooms, are traumatic, with profuse amounts of blood and other bodily fluids present. Because defibrillators are present at such scenes and are reusable, it is important that they be thoroughly cleaned between uses to avoid blood-borne pathogens and the like being passed from patients to future patients or healthcare providers.

In addition, hospitals and even different ambulances (within a single firehouse) may employ different brands and/or types of defibrillators with different layouts, button configurations, etc. Each of the different brands and/or types of defibrillators may have different cleaning procedures, requiring the users be well-versed in cleaning and maintaining many different types and/or brands of defibrillators.

SUMMARY

Aspects of embodiments of the present invention are direct toward a disposable defibrillator cover and a method of installing the same. The cover prevents and/or blocks bodily fluids, germs, and/or bacteria from transferring therethrough onto a protected defibrillator to protect subsequent users and patients from infection.

According to an embodiment of the present invention, a defibrillator and a cover adhered to the defibrillator are provided. The defibrillator includes: a case; a handle at an upper surface of the case; a display panel at a front face of the case; and a plurality of buttons at the front face of the case. The cover covers the display panel and at least some of the buttons, and the cover includes a flexible plastic film.

The cover may have an adhesive coating applied to a surface thereof.

An upper edge of the cover may be on the upper surface of the case between the front face and the handle.

A first side edge of the cover may be on a first side surface of the case, and a second side edge of the cover may be on a second side surface of the case.

The cover may not extend onto a bottom surface of the case.

The defibrillator may further include a bezel surrounding a periphery of the display panel, and the display panel may be recessed from the bezel forming a gap between the display panel and the bezel.

A portion of the cover over the gap between the display panel and the bezel may be flat.

The cover may be adhered to the display panel and to the bezel, and a portion of the cover between the portions adhered to the display panel and the bezel may be slanted with respect to the portions adhered to the display panel and the bezel.

The cover may be between 2.0 mil and 3.0 mil thick.

The cover may have dimensions of 9 inches by 12 inches.

According to another embodiment of the present invention, a method of installing a cover onto a defibrillator includes adhering the cover onto a front face of the defibrillator. The cover includes a flexible plastic film.

The method may further include adhering the cover onto a display panel on the front face of the defibrillator after adhering the cover onto the front face of the defibrillator. The display panel may be recessed from the front face of the defibrillator.

The cover may be separated from the display panel at an area adjacent a bezel. The bezel may surround a periphery of the display panel.

The method may further include adhering the cover onto an upper surface and at least one of a left side and a right side of the defibrillator.

BRIEF DESCRIPTION OF THE DRAWINGS

The above and other features and aspects of the present invention will become more apparent by describing, in detail, example embodiments thereof with reference to the attached drawings, in which.

DETAILED DESCRIPTION

The present invention will now be described more fully with reference to the accompanying drawings, in which example embodiments are shown. In the drawings, sizes and thicknesses of elements may be exaggerated for clarity. Like reference numerals in the figures denote like elements throughout, and redundant descriptions thereof may be omitted.

It will be understood that when an element is referred to as being "on," "connected to," or "coupled to" another element, it may be directly on, connected, or coupled to the other element or one or more intervening elements may also be present. When an element is referred to as being "directly on," "directly connected to," or "directly coupled to" another element, there are no intervening elements present. As used herein, the term "and/or" includes any and all combinations of one or more of the associated listed items. Further, the use of "may" when describing embodiments of the present invention relates to "one or more embodiments of the present invention."

Spatially relative terms, such as "beneath," "below," "lower," "above," "upper," "bottom," "top" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" or "over" the other elements or features. Thus, the term "below" may encompass both an orientation of above and below. The device may be otherwise oriented (rotated 90 degrees or at other orientations), and the spatially relative descriptors used herein should be interpreted accordingly.

The terminology used herein is for the purpose of describing particular example embodiments only and is not intended to limit the example embodiments described herein. As used herein, the singular forms "a" and "an" are intended to include the plural forms as well, unless the context clearly indicates otherwise. It will be further understood that the terms "includes," "including," "comprises," and/or "comprising," when used in this specification, specify the presence of stated features, steps, operations, elements, and/or components but do not preclude the presence or addition of one or more other features, steps, operations, elements, components, and/or groups thereof.

Referring to FIGS. 1-8, a defibrillator 100 and a cover 200 are provided. The defibrillator 100 may include a case 105, a handle 110 at a top (e.g., an upper surface) of the case 105, a display panel 115 on a front face 125 thereof, and a plurality of feet 145 at a bottom (e.g., a lower surface) of the case 105. Although not shown, the defibrillator 100 includes a plurality of paddles connected to the defibrillator 100 via detachable cables, and a user may hold the paddles to a patient's chest to apply an electric shock thereto.

The case 105 may have a three-dimensional rectangular shape and, in some embodiments, may have a substantially three-dimensional square shape, with corners 150 (e.g., sharp or square edges) at where the different faces (or surfaces) meet each other.

On the front face 125 of the defibrillator 100, a bezel 120 may be provided around the display panel 115. A plurality of buttons 130, 135, and 140 may be provided in the bezel 120. The buttons 130, 135, and 140 may be arranged into groups around a plurality of sides (e.g., around three sides) of the display panel 115. For example, in the embodiment shown in FIGS. 1-8, three groups of three buttons 130, 135, and 140 are shown, but the present invention is not limited thereto.

The bezel 120 may have text or images printed thereon, providing instructions to the user and/or indicating the functions of different buttons 130, 135, and 140 and/or different areas of the display panel 115.

The display panel 115 may be recessed from the bezel 120. Because the display panel 115 is recessed from the bezel 120, a gap (e.g., a step-gap or step-height gap) 116 may be formed between the display panel 115 and the bezel 120. The gap 116 may be an area susceptible to trapping bodily fluids and the like during use and may be difficult to adequately clean. If the gap 116 is not adequately cleaned between uses, the bodily fluids and the like may be allowed to remain in the gap 116 or may seep between the display panel 115 and the bezel 120 through the gap 116, and subsequent users of the defibrillator 100 may be at risk of being infected by any bloodborne pathogens or the like in the bodily fluids.

Similar to how bodily fluids may be trapped in the gap 116 between the display panel 115 and the bezel 120, bodily fluids may also become trapped between the buttons 130, 135, and 140 and the bezel 120. Due to the tolerances between the bezel 120 and the buttons 130, 135, and 140, it may be similarly difficult to clean any bodily fluids from the gaps between the buttons 130, 135, and 140 and the bezel 120, and bodily fluids may seep behind the bezel 120 between the buttons 130, 135, and 140 and the bezel 120.

The overall size of the case 105 and the arrangement of the handle 110, display panel 115, buttons 130, 135, and 140, and feet 145 may vary between different brands and/or types of defibrillators. For example, different brands and/or types of defibrillators may have different arrangements of handles, display screens, buttons, feet, etc.

In addition, a single health care entity, such as a hospital, fire department, ambulance company, etc. may have various different brands and/or types of defibrillators in their possession and/or in use. As such, it may be difficult for emergency responders and/or employees to learn, remember, and employee proper cleaning and maintenance techniques for the different defibrillators and/or notice or remember the different areas of the defibrillators that may be susceptible to collecting bodily fluids. The cover 200 is provided to provide ease of cleaning and maintenance of different defibrillators.

The cover 200 may include (or may be formed of) a flexible plastic film, for example, a flexible plastic film composed of polyvinyl chloride, polyethylene (e.g., low density polyethylene), etc. The cover 200 may be, for example, between about 2.0 mil and about 3.0 mil thick and may be about 9 inches wide by about 12 inches long (or tall). For example, the 9 inch dimension of the cover 200 may be from one side of the case 105 to the opposite side of the case 105, and the 12 inch dimension of the cover 200 may be from the top of the case 105 where the handle 110 is arranged to the bottom of the case 105 where the feet 145 are arranged.

The cover 200 may be clear so that the display panel 115, the buttons 130, 135, and 140, and any text and/or images on the bezel 120 remain visible to the user after the cover 200 is applied to the defibrillator 100. Further, the plastic material is impermeable to bodily fluids, germs, and/or bacteria, and therefore, any bodily fluids, germs, and/or bacteria on the cover 200 may not be transmitted therethrough onto the covered surface(s) of the defibrillator 100. The plastic material may have a strength such that a user may puncture or tear the plastic material by hand or with a cutting tool for ease of installation, as is further described below.

One side of the cover 200 (e.g., a rear or bottom side of the cover 200) may have an adhesive coating thereon. The adhesive coating may be an optically clear adhesive (OCA) and/or a pressure sensitive adhesive (PSA). The adhesive coating may be any suitable adhesive that adheres to the material of the defibrillator 100 (e.g., plastic). For example, the adhesive coating may be a water-based acrylic adhesive. The adhesive coating may not adhere to (e.g., may not strongly adhere to) the cover 200 such that the surface of the cover 200 having the adhesive coating will not strongly adhere to the other surface of the cover 200 not having the adhesive coating thereon. For example, when the surface of the cover 200 having the adhesive coating thereon adheres to the other surface of the cover 200, such as when the cover 200 falls onto itself during installation or the like, the user can easily pull the different surfaces of the cover 200 apart without damaging the cover 200.

In other embodiments, the cover 200 may use the "static cling" phenomenon to be adhered to the defibrillator 100 without using an adhesive coating. As is known by those skilled in the relevant art, the "static cling" phenomenon occurs when materials with similar cohesive force are placed into contact with each other.

The cover 200 may be formed (e.g., manufactured) as a long sheet of the plastic material having the adhesive coating on one side thereof. The long sheet may be perforated at regular intervals corresponding to the length of the cover 200. The long sheet may be in a roll so that a plurality of covers 200 may be compactly and easily shipped. As needed, the user may roll out a single cover 200 from the roll of covers and separate the cover 200 from the roll at the perforated portion, thereby providing a single cover 200 to be adhered to the defibrillator 100 while the remaining covers remain part of the roll. However, in other embodiments, the covers 200 may be individually formed and shipped for easier installation.

Figure 8:
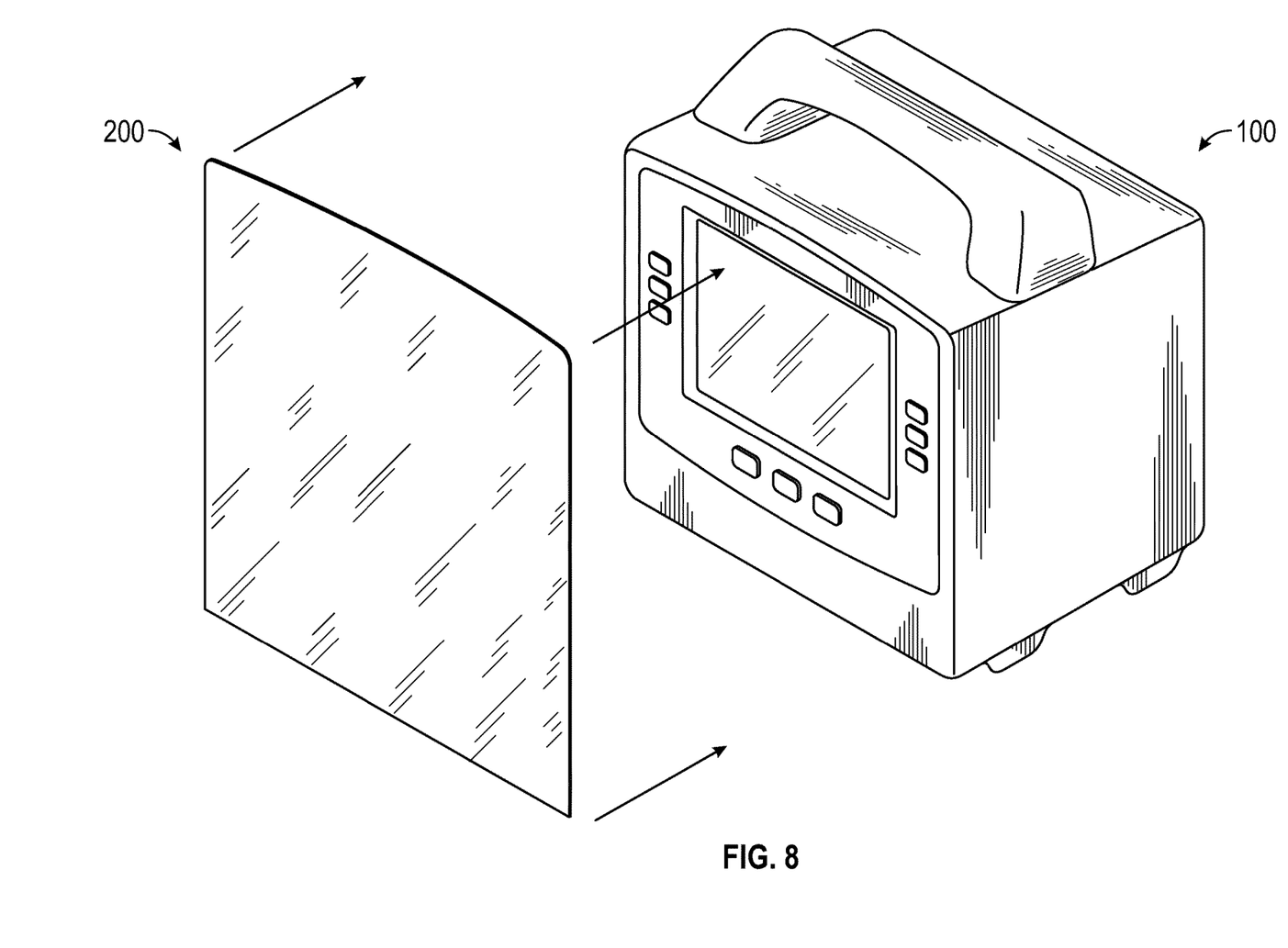
FIG. 8 is a perspective view of an act of adhering the cover onto the defibrillator.

Referring to FIG. 8, prior to being installed onto the defibrillator 100, the cover 200 may be substantially flat. For example, the cover 200 may start as a flat sheet of flexible plastic material (e.g., a flexible plastic film). The arrows in FIG. 8 indicate the installation direction of the cover 200 onto the defibrillator 100. As shown in FIG. 8, a user installs the cover 200 onto the front face 125 of the defibrillator 100 in a direction normal to the front face 125. The user may install the cover 200 flat onto the front face 125 of the defibrillator and press the cover 200 onto the defibrillator 100 from the center of the front face 125 to the edges thereof, with any remaining material being pressed onto side surface(s) of the defibrillator 100. The present invention is not limited thereto, and in other embodiments, the user may install the cover 200 from one edge of the front face 125 toward other edges thereof, as further described below.

The cover 200 may extend from the front face 125 of the defibrillator 100 onto an upper surface, a lower surface, and first and/or second (e.g., left and/or right) side surfaces of the defibrillator 100. The present invention is not limited thereto, however, and in some embodiments, the cover 200 may not extend onto all of or even any of these sides. For example, referring to FIG. 6, the cover 200 may not extend onto the lower surface of the defibrillator 100 adjacent the feet 145.

Figure 5:
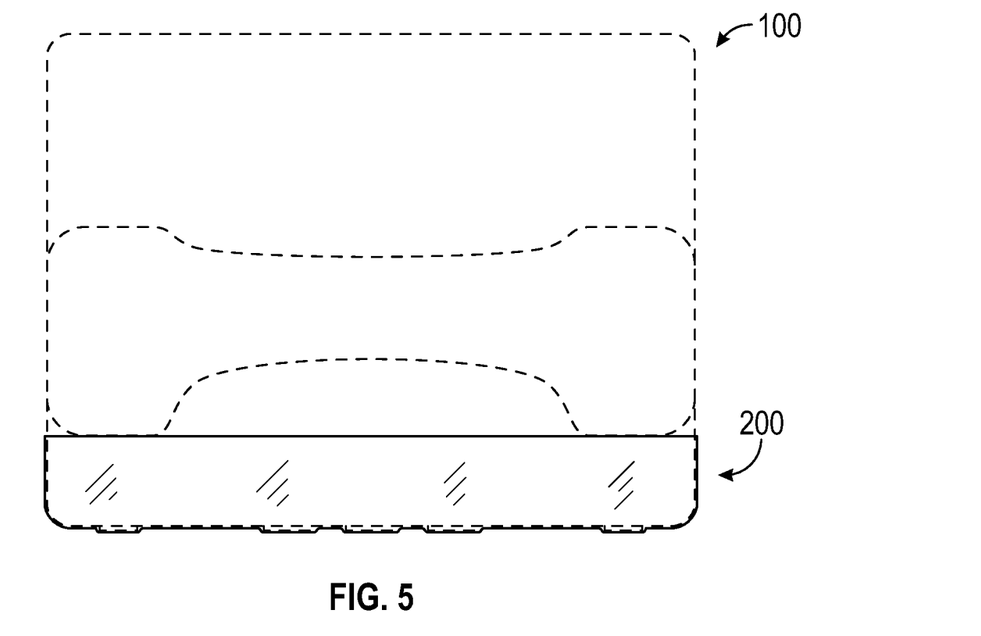
FIG. 5 is a top view of the defibrillator with cover shown in FIG. 1.
Figure 6:
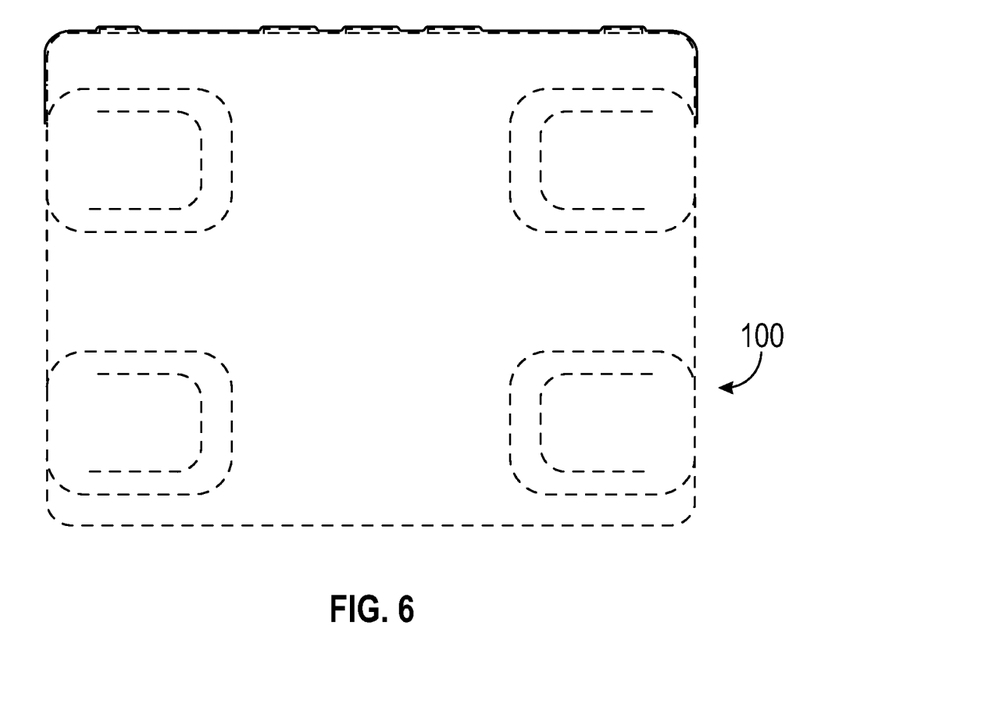
FIG. 6 is a bottom view of the defibrillator with cover shown in FIG. 1.

Referring to FIG. 5, the cover 200 may extend on the upper surface of the defibrillator 100 to a point adjacent the handle 110 (e.g., to a point between the front face 125 and the handle 110). For example, the cover 200 may not extend onto the handle 110 but may extend to be adjacent the handle 110. In some embodiments, however, the cover 200 may extend over the handle 110, and the user may puncture the cover 200 to access the handle 110 after the cover 200 is applied thereto.

Figure 1:
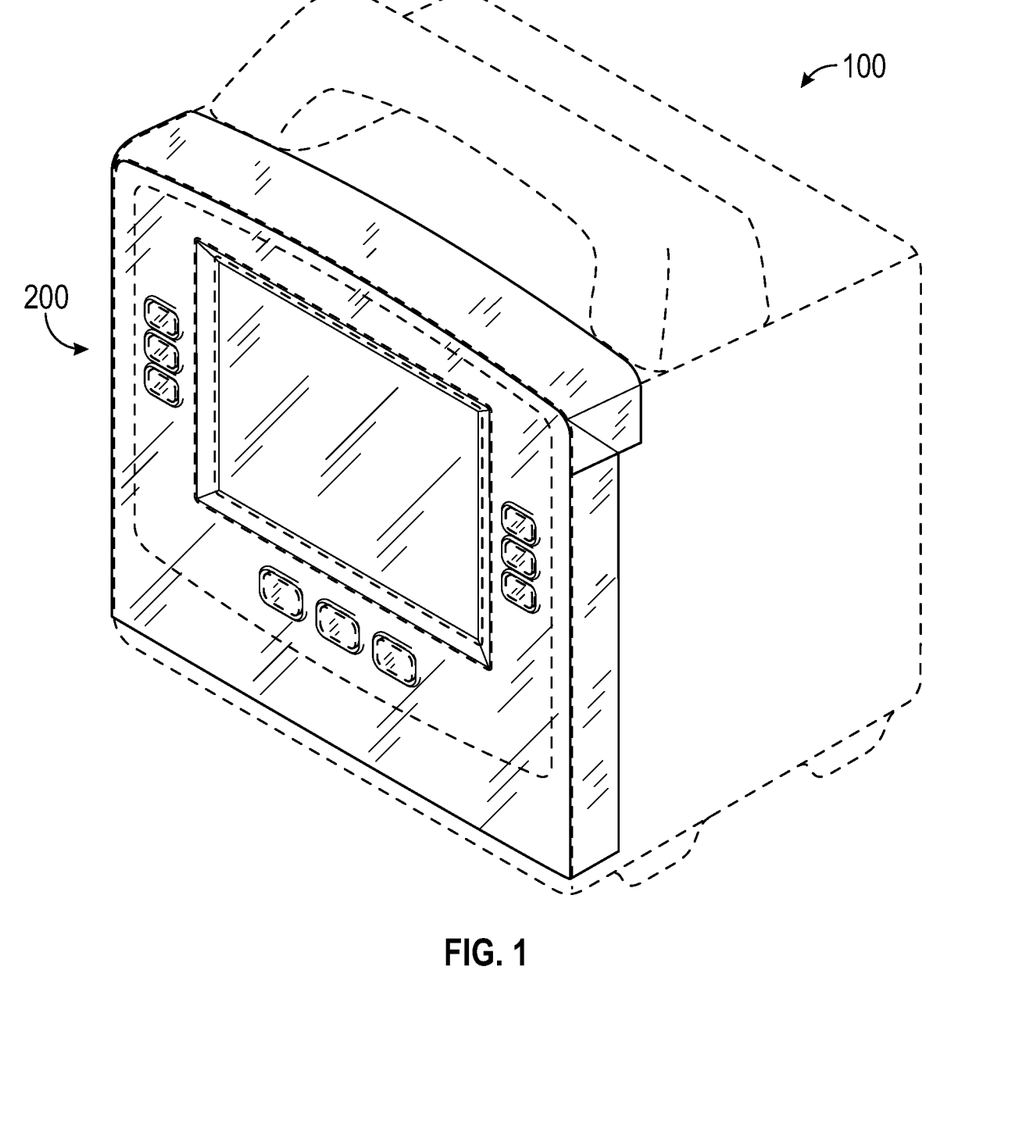
FIG. 1 is a perspective view of a defibrillator with a cover adhered thereto, with the defibrillator shown in broken lines.
Figure 2:
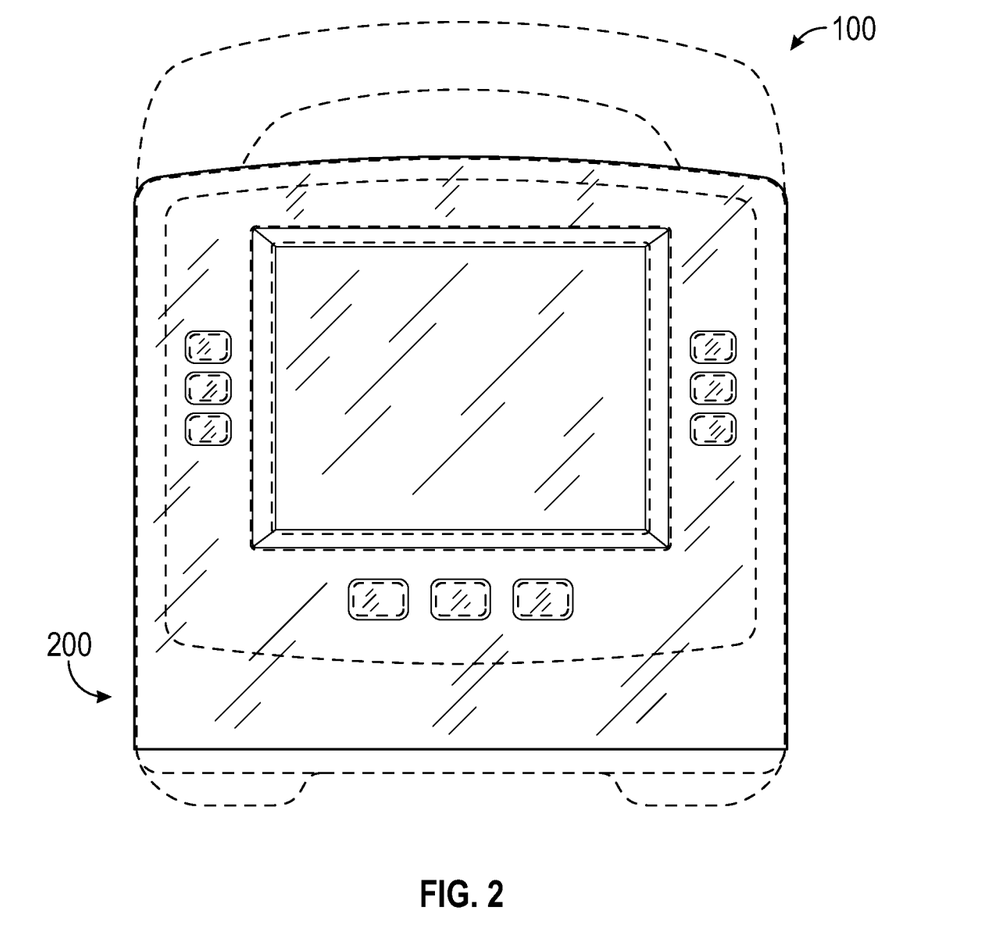
FIG. 2 is a front view of the defibrillator with cover shown in FIG. 1.
Figure 3:
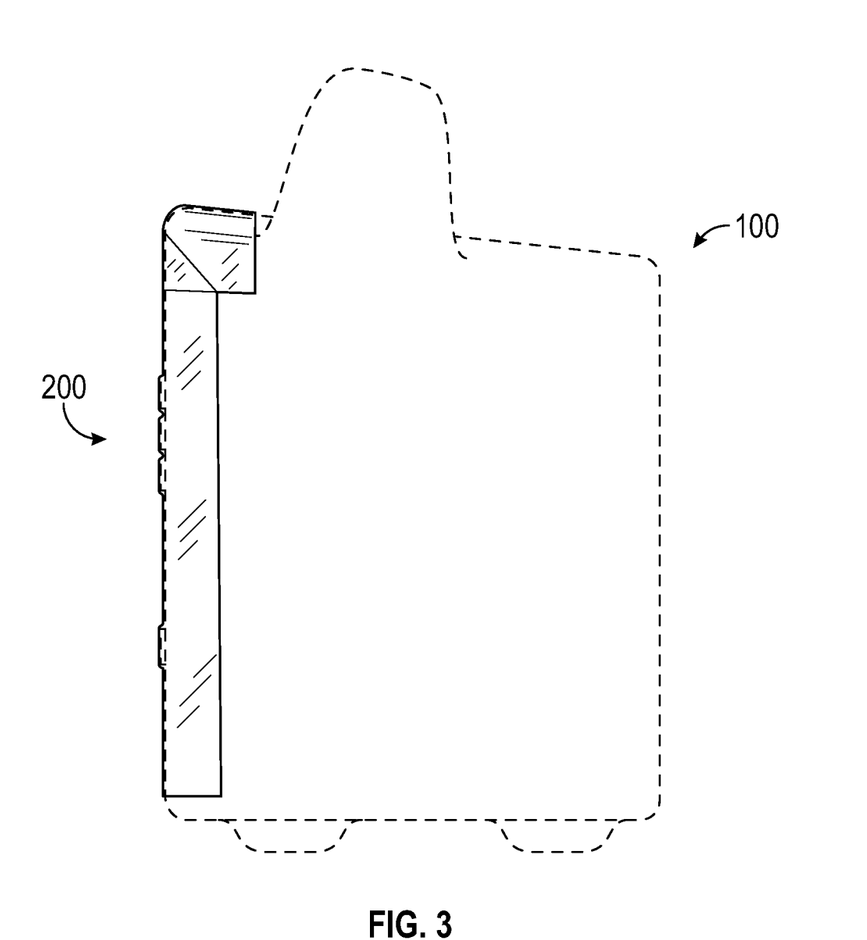
FIG. 3 is a left-side view of the defibrillator with cover shown in FIG. 1.
Figure 4:
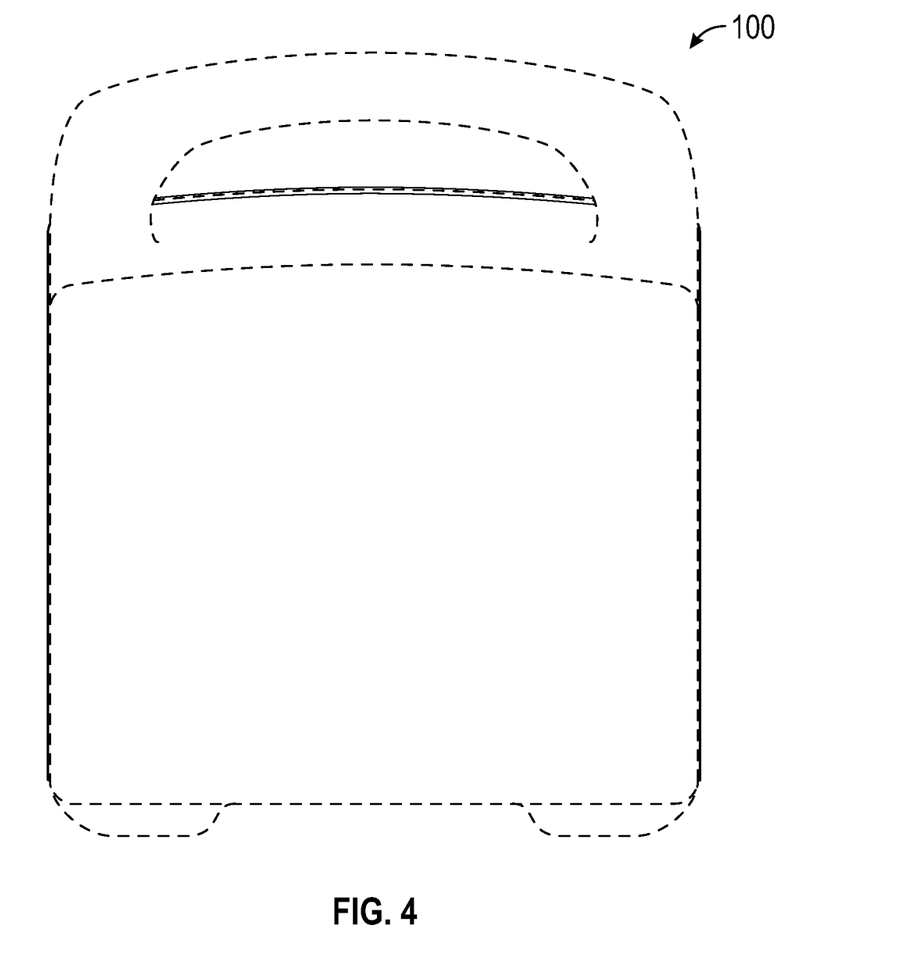
FIG. 4 is a rear view of the defibrillator with cover shown in FIG. 1.
Figure 7:
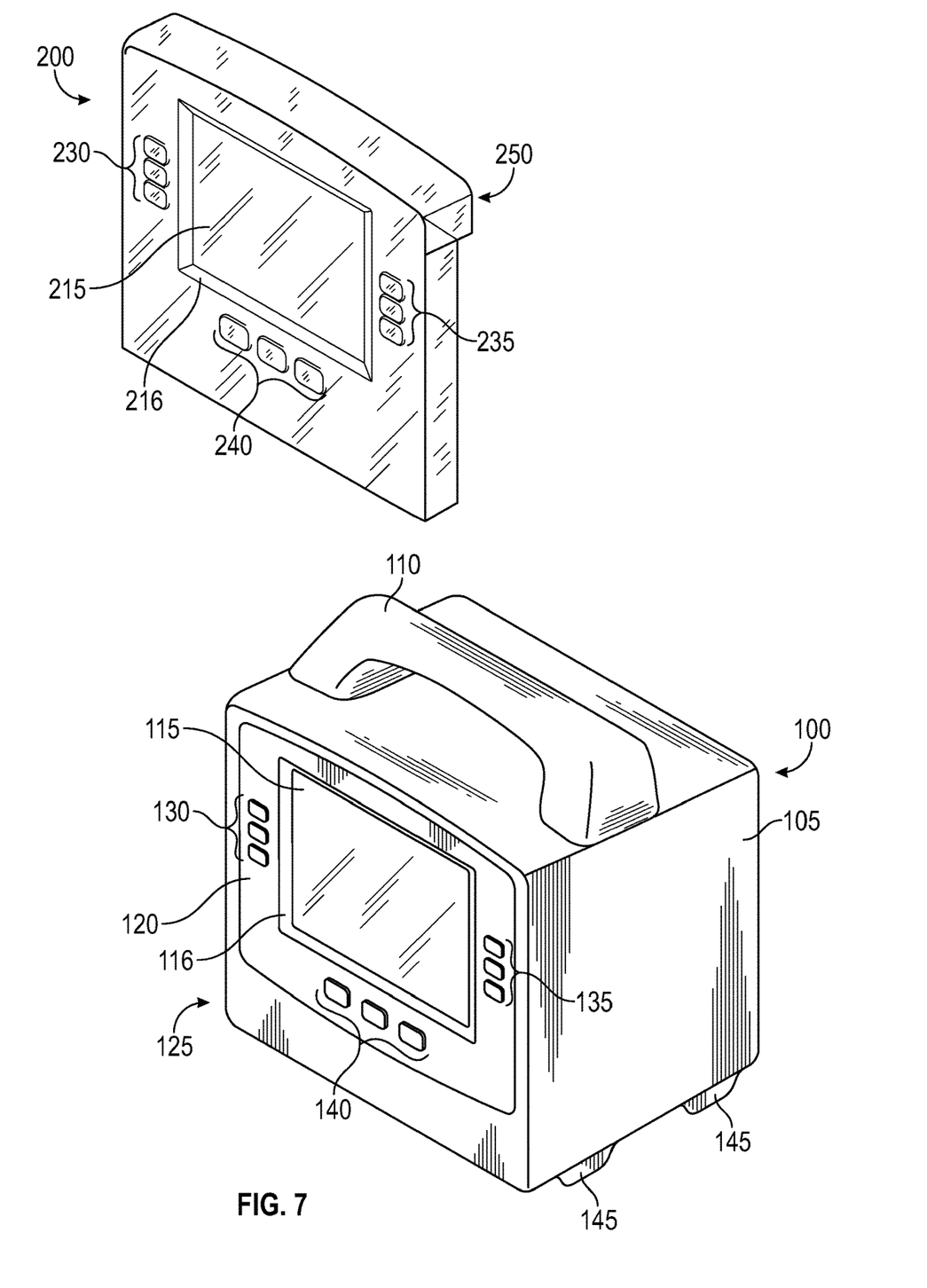
FIG. 7 is a perspective of the defibrillator with cover shown in FIG. 1 in a separated state, with the defibrillator shown in solid lines.

Because the cover 200 is a generally rectangular or square film, it may bunch 250 at the corners 150 between the different surfaces of the defibrillator 100. Referring to FIGS. 1 and 7, the cover 200 may be folded at the corners 150 of the defibrillator 100 to prevent or mitigate bunching 250. For example, during installation, a user may first adhere the cover 200 to the upper surface or one of the left and right surfaces of the defibrillator 100 and may then adhere the cover 200 to the other of the upper surface or the left and right surfaces. In this way, the cover 200 may overlap itself at the corners 150 of the defibrillator, and the corners 250 of the cover 200 may lie substantially flat on the defibrillator 100 without any reliefs (e.g., notches or slits) being cut into the cover 200. However, in some embodiments, the corners of the cover 200 may be cut to provide reliefs, allowing the corners 250 of the cover 200 to lie flatter onto the defibrillator 100 at the corners 150 thereof.

In some embodiments, in which the display panel 115 does not include a touch panel (e.g., is not a touch screen), the cover 200 may not be pressed onto the display panel 115. For example, because the display panel 115 is recessed from the bezel 120, the cover 200 may extend over the display panel 115 without contacting the display panel 115. In other embodiments, such as when the display panel 115 of the defibrillator 100 includes a touch panel (e.g., is a touch screen), a portion 215 of the cover 200 may be adhered to the display panel 115. When the portion 215 of the cover 200 contacts the display panel 115, the cover 200 does not closely fit into the gap 116 between the bezel 120 and the display panel 115. For example, a flat or slanted portion 216 of the cover 200 bridges the gap 116 between the display panel 115 and the bezel 120 and provides a flat or slanted portion 216 extending over the gap 116 without contacting either the bezel 120 or the display panel 115 at the gap 116. This way, any bodily fluid that lands on the cover 200 does not get trapped into a corresponding gap or corner in the cover 200 but instead sits on the flat or slanted portion 216 of the cover 200 for easy cleaning.

Similarly, the cover 200 extends over the buttons 130, 135, and 140 and prevents bodily fluids or the like from getting into the openings between the buttons 130, 135, and 140 and the bezel 120. Also similar to how the cover 200 bridges the gap 116 between the bezel 120 and the display panel 115, the cover 200 also bridges the openings between the buttons 130, 135, and 140 and the bezel 120. That is, portions 230, 235, and 245 of the cover 200 respectively extend over the buttons 130, 135, and 140 and the bezel 120 without extending into the openings between the buttons 130, 135, and 140 and the bezel 120, thereby allowing bodily fluids to be easily cleaned from the cover 200.

Hereinafter, a method of installing the cover 200 onto the defibrillator 100 will be described. First, when the cover 200 is provided in a roll with a plurality of other covers 200, one of the covers 200 is separated from the roll. To this end, a user may tear the cover 200 at a pre-perforated line or may cut the cover 200 to a desired length by using any suitable cutting instrument, such as scissors or the like.

Then the cover 200 is positioned in front of (or over) the front face 125 of the defibrillator 100. The user then adheres the cover 200 onto the front face 125 of the defibrillator 100. To this end, the user may align one edge of the cover 200 with a particular area of the defibrillator 100 and then adhere the remainder of the cover 200 onto the defibrillator 100 from the aligned edge to an opposite edge. For example, the user may align an edge of the cover 200 with an area of the upper surface of the defibrillator 100 between the handle 110 and the front face 125 and may then adhere the cover 200 in a top-down manner from the upper surface over the front face 125 with any remaining portion of the cover 200 being adhered to the bottom surface of the defibrillator 100. In another embodiment, the user may align an edge of the cover 200 onto a left or right side surface of the defibrillator 100 and adhere the cover 200 from the aligned edge onto the front face 125, with any remaining portion of the cover 200 being adhered onto the other of the left or right side surface of the defibrillator 100.

The user then adheres the cover 200 to the uncovered side(s) of the defibrillator 100. For example, when the user applies the cover 200 to the defibrillator 100 from the upper surface toward the lower surface thereof, the user may then adhere the cover 200 to the left and right sides of the defibrillator 100. As another example, when the user applies the cover 200 to the defibrillator 100 from the left side toward the right side thereof (or from the right side toward the left side thereof), the user may then adhere the cover 200 to the upper and/or lower surfaces of the defibrillator 100. In this way, the bunching 250 of the cover 200 at the corners 150 of the defibrillator 100 may be minimized or reduced, reducing the risk that the cover 200 is inadvertently removed from the defibrillator 100 or that bodily fluids or the like seep behind the cover 200 at the corners 150/250.

Then the user may then push on the cover 200 to securely adhere it to the front face 125 of the defibrillator 100. Due to the tension in the cover 200, however, the cover 200 may not adhere to (e.g., may not adhere to the entire surface of) the display panel 115. Instead, the cover 200 may adhere to only the center portion of the display panel 115 and may be separated from the display panel 115 near the gap 116. The tension in the cover 200 may provide a smooth transition from the recessed display panel 115 to the bezel 120, forming the slanted portion 216 that extends over the gap 116 between the display panel 115 and the bezel 120. In some embodiments, the cover 200 may not contact the display panel 115 at all, providing a flat surface over the display panel 115 at the height of the bezel 120. The user may also push the cover 200 to securely adhere it around the edges of the buttons 130, 135, and 140, forming corresponding raised portions 230, 235, and 240 of the cover 200.

After use or when the cover 200 is found to be degraded, such as when the edges of the cover 200 begin to peel away from the defibrillator 100, the user may remove the cover 200 from the defibrillator 100 and throw it away. Then, the user may adhere another cover 200 to the defibrillator 100. In this way, the defibrillator 100 may be rapidly protected from bodily fluids and, when the defibrillator 100 is exposed to bodily fluids, a substantial cleaning effort may be avoided by simply replacing the cover 200.

Further, because the cover 200 may have a size of about 9 inches by about 12 inches. However, because the cover 200 may not be sized to fit any particular type and/or brand of defibrillator, one health care entity can apply the cover 200 to various different types and/or brands of defibrillators within its possession, preventing the health care entity from needing to purchase numerous different type- or brand-specific covers for different defibrillators. That is, because the cover 200 covers a front face 125 of the defibrillator 100 and any excess portions of the cover 200 are adhered to the side surfaces of the defibrillator 100, the cover 200 may be applied to different size defibrillators with the primary difference between installations being the amount of excess cover 200 that is adhered to side surfaces of the defibrillators.

While the present invention has been particularly shown and described with reference to some example embodiments thereof, it will be understood by those of ordinary skill in the art that various changes in form and details may be made therein without departing from the spirit and scope of the present invention as set forth in the following claims and their equivalents.

What is claimed is:

1. A defibrillator and an adhesive cover combined with the defibrillator,
    the adhesive cover comprising a flexible plastic film and
        a pressure-sensitive adhesive on one side of the flexible plastic film; and
    the defibrillator comprising:
        a case;
        a handle at an upper surface of the case;
        a display panel comprising a display screen at a front face corresponding to a front surface of the case;
        a bezel surrounding a periphery of the display panel at the front face of the case, the display panel being recessed from the bezel forming a gap between the display panel and the bezel; and
        a plurality of buttons at the front face of the case,
    wherein the adhesive cover is adhered to and covers the display screen, the bezel, all of the buttons at the front face, and an area of the front face between at least some of the buttons and the display screen,
    wherein a portion of the adhesive cover between the portions adhered to the display panel and the bezel is slanted with respect to the portions adhered to the display panel and the bezel, and
    wherein the adhesive cover extends from the front surface of the case to an adjacent surface of the case that is a surface other than the front surface and is adhered to the adjacent surface of the case to prevent introduction of foreign material between the adhesive cover and the front surface of the case.

2. The defibrillator and the adhesive cover combined with the defibrillator of claim 1, wherein an upper edge of the adhesive cover is on the upper surface of the case between the front face and the handle.

3. The defibrillator and the adhesive cover combined with the defibrillator of claim 2, wherein a first side edge of the adhesive cover is on a first side surface of the case, and a second side edge of the adhesive cover is on a second side surface of the case.

4. The defibrillator and the adhesive cover combined with the defibrillator of claim 3, wherein the adhesive cover does not extend onto a bottom surface of the case.

5. The defibrillator and the adhesive cover combined with the defibrillator of claim 1, wherein the adhesive cover is between 2.0 mil and 3.0 mil thick.

6. The defibrillator and the adhesive cover combined with the defibrillator of claim 5, wherein the adhesive cover has dimensions of 9 inches by 12 inches.

7. The defibrillator and the adhesive cover combined with the defibrillator of claim 1, wherein the defibrillator comprises a plurality of the buttons at the front face,
    wherein the adhesive cover covers an entirety of the front face of the case, and
    wherein the adhesive cover is adhered to each of the plurality of buttons at the front face and to an area of the front face between adjacent ones of the plurality of buttons at the front face.

8. A method of using a defibrillator with an adhesive cover, the defibrillator comprising a display panel recessed from a bezel surrounding the display panel, the adhesive cover comprising a flexible plastic film and a pressure-sensitive adhesive on one side of the flexible plastic film, the method comprising:
- adhering the adhesive cover onto a front face corresponding to a front surface of the defibrillator, over a button at the front face, to a display screen of the display panel at the front face, to the bezel surrounding a periphery of the display panel such that a portion of the adhesive cover between the portions adhered to the display panel and the bezel is slanted with respect to the portions adhered to the display panel and the bezel;
- adhering the adhesive cover onto an adjacent surface of the defibrillator that is a surface other than the front surface to prevent introduction of foreign material between the adhesive cover and the front surface;
- using the defibrillator to apply an electric shock through paddles connected to the defibrillator while the adhesive cover is adhered to the defibrillator; and
- removing the adhesive cover from the defibrillator after the using the defibrillator to apply the electric shock.

9. The method of claim 8, wherein the display panel is recessed from the front face of the defibrillator.

10. The method of claim 9, wherein the adhesive cover is not adhered to the display panel at an area directly adjacent the bezel.

11. The method of claim 9, further comprising adhering the adhesive cover onto an upper surface and at least one of a left side and a right side of the defibrillator.

12. The method of claim 8, further comprising adhering excess portions of the adhesive cover to a left side surface and a right side surface of the defibrillator.

13. The method of claim 12, wherein the defibrillator comprises a plurality of the buttons at the front face,
- wherein the adhesive cover covers an entirety of the front face, and
- wherein the adhesive cover is adhered to each of the plurality of buttons at the front face and to an area of the front face between adjacent ones of the plurality of buttons at the front face.

* * * * *